United States Patent [19]

Tada et al.

[11] 4,163,018

[45] Jul. 31, 1979

[54] PROCESS FOR PREPARING METAL SALTS OF ALKYL PHOSPHATES

[75] Inventors: Fusao Tada, Toyonaka; Jajimu Shimizu, Nara; Tsutomu Asaoka, Kishiwada; Fuminori Matsumoto, Sakai, all of Japan

[73] Assignee: Sakai Chemical Industry Company, Ltd., Japan

[21] Appl. No.: 860,408

[22] Filed: Dec. 13, 1977

[30] Foreign Application Priority Data

Dec. 18, 1976 [JP] Japan .................................. 51-153175

[51] Int. Cl.² .............................................. C07F 3/06
[52] U.S. Cl. .............................. 260/429.9; 260/448 R; 260/983
[58] Field of Search ................. 260/429.9, 448 R, 983

[56] References Cited

U.S. PATENT DOCUMENTS

| | | | |
|---|---|---|---|
| 2,329,707 | 9/1943 | Farrington et al. | 260/429 |
| 2,346,155 | 4/1944 | Denison et al. | 252/32 |
| 2,416,985 | 3/1947 | Farrington et al. | 260/448 R |
| 2,885,417 | 5/1959 | Heyden | 260/448 R X |
| 2,953,479 | 9/1960 | Heyden et al. | 260/448 R X |
| 3,494,949 | 2/1970 | Monroe et al. | 260/448 R |

Primary Examiner—Helen M. S. Sneed
Attorney, Agent, or Firm—Jones, Tullar & Cooper

[57] ABSTRACT

A process for preparing metal salts of alkyl phosphate of either one of the formulae:

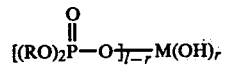

and

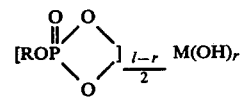

which comprises reacting an alkyl phosphate of either one of the formulae:

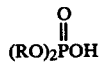

and

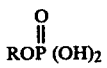

in the form of its alkali metal salt with a metal salt of the formula: $M_nX_m$ in an aqueous medium at a temperature of from about 50° to 80° C. (wherein R is an alkyl group of not less than 12 carbon atoms, M is an alkaline earth metal, aluminum or zinc, X is halogen ion, sulfate ion or nitrate ion, l is an integer corresponding to the atomic valency of M, r is an integer of 0, 1 or 2, m is an integer of 1, 2 or 3 and n is an integer of 1 or 2).

4 Claims, No Drawings

PROCESS FOR PREPARING METAL SALTS OF ALKYL PHOSPHATES

The present invention relates to metal salts of alkyl phosphates in fine powders, and their production and use.

Metal salts of alkyl phosphates representable by either one of the formulae:

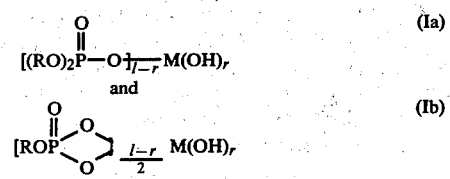

wherein R is an alkyl group of not less than 12 carbon atoms (preferably of from 12 to 20 carbon atoms), M is an alkaline earth metal (e.g. magnesium, calcium, barium), aluminum or zinc, l is an integer corresponding to the atomic valency of M and r is an integer of 0, 1 or 2, are known and useful as additives, particularly as heat stabilizers and oxidation stabilizers, to various resins and plastics such as vinyl chloride resins, vinyl acetate-ethylene copolymers and acrylonitrile-butadiene-styrene resins.

The said metal salts of alkyl phosphates (Ia) or (Ib) have heretofore been produced by various procedures, among which typical examples are as follows:

---
Procedure A (U.S. Pat. No. 3,396,144)

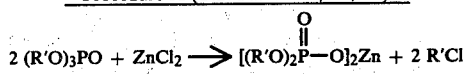

Procedure B (Japanese Patent Publication (examined) No. 12646/1967)

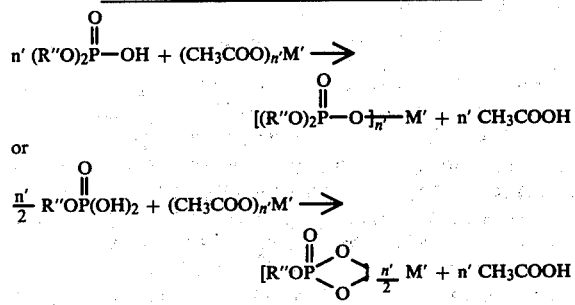

---
(R': an alkyl group of 1 to 8 carbon atoms)
(R": a hydrocarbon group of not less than 6 carbon atoms;
M': a metal other than alkali metal;
n': an interger)

However, these conventional procedures have some certain drawbacks. For instance, the following disadvantages are pointed out on the said Procedure A: (a) when the number of carbon atoms in R' is relatively large, a high temperature is required for the reaction, and it is practically difficult to eliminate R'Cl without loss of the desired product; (b) the starting alkyl phosphate is expensive, while the by-produced R'Cl does have only limited use; (c) the starting $ZnCl_2$ is required to be anhydrous; (d) purification of the desired product is difficult, and the desired product of high purity is hardly obtainable; (e) the desired product is hardly obtainable in fine powders, etc.

Further, for instance, the said Procedure B has the following disadvantages: (a) the starting metal acetate is relatively expensive and may often be not easily available at an industrial scale; (b) the reaction requires a high temperature and a long time, and the elimination of the by-produced acetic acid without loss of the desired product is quite difficult; (c) the desired product is not readily purified, and it is hardly obtainable in high purity; (d) the desired product is not obtainable in fine powders, etc.

In addition, the desired products in the conventional procedures are frequently colored, and their yields are relatively low. Particularly, those products are usually obtained in the form of viscous liquid or blocked solid and hardly obtainable in fine powders, and their handling may be troublesome.

As the result of the extensive study, it has now been found that the reaction of alkyl phosphates in the form of their alkali metal salts with alkaline earth metal, aluminum or zinc salts of mineral acids in an aqueous medium at a certain range of temperature can afford the objective metal salts of alkyl phosphates (Ia) or (Ib) in fine powders with excellent yields and high purities at low costs, and further that the subsequent operations of filtration, water washing and drying thereto at the limited temperature can provide the product as a soft powder cake, which may again be pulverized, if necessary, into extremely fine powder form. It is particularly notable that the products in such process are never colored. The present invention is based on this finding.

According to the present invention, the metal salts of alkyl phosphates (Ia) or (Ib) are obtainable by reacting the corresponding alkyl phosphates of either one of the formulae:

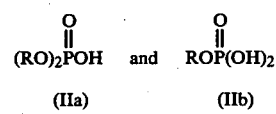

wherein R is as defined above in the form of their alkali metal salts with metal salts of the formula: $M_nX_m$ (III) wherein M is as defined above, X is halogen ion, sulfate ion or nitrate ion, m is an integer of 1, 2 or 3 and n is an integer of 1 or 2, in an aqueous medium at a temperature of about 50 to 80° C.

The process of this invention is carried out in two steps, i.e. the conversion of the alkyl phosphate (IIa) or (IIb) into its alkali metal salt and the reaction of the resulting alkali metal salt with the metal salt (III). When, for instance, the alkali metal salt is sodium and the metal salt is zinc, the process is representable by the following formulae:

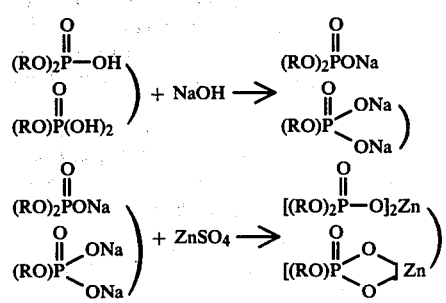

In the starting alkyl phosphate (IIa) or (IIb), R is required to be not less than 12 carbon atoms. When the number of carbon atoms is lesser, the ultimate product is in a paste-like state and includes water-soluble materials in most cases. Thus, a high yield of the product is not assured, and the recovery of the product is troublesome.

The conversion in the first step may be accomplished by treating the alkyl phosphate (IIa) or (IIb) with an alkali metal hydroxide such as sodium hydroxide or potassium hydroxide in an aqueous medium, generally at a temperature of about 60 to 90° C. For instance, the alkali metal hydroxide may be added to a suspension of the alkyl phosphate (IIa) or (IIb) in water. Alternatively, the alkyl phosphate (IIa) or (IIb) may be added to a solution of the alkali metal hydroxide in water.

The reaction in the second step may be effected by treating the alkali metal salt of the alkyl phosphate (IIa) or (IIb) prepared as above with the metal salt (III) in an aqueous medium at a temperature of about 50 to 80° C. The concentrations of the alkali metal salt and of the metal salt in the aqueous medium are not critical, but it is generally favorable to keep the concentration of the alkali metal salt below about 5% by weight. During the reaction, the temperature should be kept between about 50 and 80° C. When the temperature is higher than the upper limit, the product is not obtainable in fine powders. When the temperature is lower than the lower limit, a long time is needed for completion of the reaction, which is disadvantageous from the industrial viewpoint. The recovery of the product from the reaction mixture, for instance, by filtration, water washing, drying and pulverizing should be carried out under the temperature of not higher than 80° C. and the maintenance of this temperature limit is necessary for obtaining the product in fine powders; otherwise, the product is pulverized in not so fine state.

The product in the process of this invention is the metal salt of alkyl phosphate (Ia) or (Ib). When M is any metal other than aluminum, r is usually zero; i.e. free hydroxyl groups are not included. When M is aluminum, r is varied from 0 to 2 depending on the amount of the metal salt (III) as employed. A higher amount of the metal salt (III) may afford the product (Ia) or (Ib) wherein r is closer to 2. In case of the metal salt (III) being higher, it is preferable to make present a larger amount of the alkali metal hydroxide in the reaction system.

The product of this invention is obtainable in fine powders and shows a good dispersibility into resins, plastics and other materials such as grease. Because of this reason, it produces a more excellent technical effect than the one produced by any conventional procedure when used as an additive such as a lubricant, a heat stabilizer or a weathering resistance improver.

Besides, the process of this invention is quite advantageous in producing the metal salt of alkyl phosphate (Ia) or (Ib) in fine powders (having a large apparent specific volume) with an excellent yield and a high purity from cheaper and readily available starting materials by simple operations.

Presently preferred and practical embodiments of the present invention are illustratively shown in the following examples, wherein % is by weight. The apparent specific volume was determined according to JIS (Japanese Industrial Standard) K5101.

EXAMPLE I

Water (20 L) was added to cetyl phosphate (molar ratio of diester/monoester=1/1; acid value, 194 mg KOH/g) (1 kg) while heating at 70° C., whereby the cetyl phosphate was dispersed uniformly. An aqueous solution of sodium hydroxide (500 g/L) (278 ml) was dropwise added to the mixture while keeping the said temperature. When the addition was finished, the mixture showed a pH of about 11. Further, stirring was continued at 70° C. for 60 minutes. An aqueous solution of barium chloride (200 g/L) (1825 ml) was gradually added thereto at a temperature of 70 to 80° C. After the addition was finished, the mixture was stirred at about 70° C. for 30 minutes. On confirming that the remaining barium ion became constant, the reaction was finished. The product was collected, washed with water, filtered, dried at 70° C. for 76 hours and pulverized in a mortar to give barium cetyl phosphate (1154 g). Yield, 93.5%. M.P., 174 to 183° C. Apparent specific volume, 3.6 ml/g. Elementary analysis: calcd., P=5.8%, Ba=19.2%; found, P=5.9%, Ba=18.0%.

EXAMPLE 2

Water (19 L) was added to lauryl phosphate (molar ratio of diester/monoester=1/1; acid value, 240.2 mg KOH/g) (1 kg) while heating at 60° C., whereby the lauryl phosphate was dispersed uniformly. An aqueous solution of sodium hydroxide (300 g/L) (571 ml) was dropwise added to the mixture while keeping the said temperature. When the addition was finished, the mixture showed a pH of about 11. Further, stirring was continued at 60° C. for 60 minutes. An aqueous solution of calcium chloride (300 g/L) (802 ml) was gradually added thereto at a temperature of 50 to 60° C. After the addition was finished, the mixture was stirred at about 55° C. for 60 minutes. On confirming that the remaining calcium ion became constant, the reaction was finished. The product was collected, washed with water, filtered, dried at 70° C. for 76 hours and pulverized in a mortar to give calcium lauryl phosphate (1031 g). Yield, 95.2%. Decomposition point, >230° C. Apparent specific volume, 4.0 ml/g. Elementary analysis: calcd., P=8.2%, Ca=8.0%; found, P=8.3%, Ca=7.8%.

EXAMPLE 3

Water (20 L) was added to stearyl phosphate (molar ratio of diester/monoester=1/0.25; acid value, 121.9 mg KOH/g) (1 kg) while heating at 85° C., whereby the stearyl phosphate was dispersed uniformly. An aqueous solution of sodium hydroxide (500 g/L) (174 ml) was dropwise added to the mixture while keeping the said temperature. When the addition was finished, the mixture showed a pH of about 11. Further, stirring was continued at 85° C. for 60 minutes. An aqueous solution of calcium chloride (300 g/L) (408 ml) was gradually added at a temperature of 60° to 70° C. After the addition was finished, the mixture was stirred at 60° C. for 90 minutes. On confirming that the remaining calcium ion in water became constant, the reaction was finished. The product was collected, washed with water, filtered, dried at 75° C. for 72 hours and pulverized in a mortar to give calcium stearyl phosphate (1011 g). Yield, 97%. M.P., 110° to 118° C. Apparent specific volume, 3.5 ml/g. Elementary analysis: calcd., P=5.4%, Ca=4.2%; found, P=5.3%, Ca=4.1%.

EXAMPLE 4

Water (17 L) was added to stearyl phosphate (molar ratio of diester/monoester=1/7.7; acid value, 278.6 mg KOH/g) (1 kg) while heating at 70° C., whereby the stearyl phosphate was dispersed uniformly. An aqueous solution of sodium hydroxide (500 g/L) (398 ml) was dropwise added to the mixture while keeping the said temperature. When the addition was finished, the mixture showed a pH of about 11. Further, stirring was continued at 70° C. for 60 minutes. An aqueous solution of calcium nitrate (200 g/L) (2083 ml) was gradually added at a temperature of 60° to 70° C. After the addition was finished, the mixture was stirred at 60° C. for 60 minutes. On confirming that the remaining calcium ion in water became constant, the reaction was finished. The product was collected, washed with water, filtered, dried at 75° C. for 72 hours and pulverized by the aid of a hammer mill to give calcium stearyl phosphate (1029 g). Yield, 94%. M.P., >250° C. Apparent specific volume, 5.5 ml/g. Elementary analysis: calcd, P=7.5%, Ca=9.1%; found, P=7.3%, Ca=9.0%.

EXAMPLE 5

Water (19 L) was added to stearyl phosphate (molar ratio of diester/monoester=1/2.7; acid value, 231.7 mg KOH/g) (1 kg) while heating at 70° C., whereby the stearyl phosphate was dispersed uniformly. An aqueous solution of sodium hydroxide (500 g/L) (331 ml) was dropwise added to the mixture while keeping the said temperature. When the addition was finished, the mixture showed a pH of about 11.5. An aqueous solution of magnesium sulfate (300 g/L) (846 ml) was gradually added thereto at a temperature of 60° to 70° C. After the addition was finished, the mixture was stirred at 60° C. for 90 minutes. On confirming that the remaining magnesium ion in water became constant, the reaction was finished. The product was collected, washed, dried at 75° C. for 72 hours and then pulverized by the aid of a hammer mill to give magnesium stearyl phosphate (1014.1 g). Yield, 97%. M.P., 210° to 215° C. Apparent specific volume, 5.0 ml/g. Elementary analysis: calcd., P=7.1%, Mg=4.8%; found, P=7.0%, Mg=4.6%.

EXAMPLE 6

Water (88 L) was added to stearyl phosphate (molar ratio of diester/monoester=1/2.7; acid value, 232 mg KOH/g) (5 kg) while heating at 90° C., whereby the stearyl phosphate was dispersed uniformly. An aqueous solution of potassium hydroxide (300 g/L) (3862 ml) was dropwise added to the mixture while keeping the said temperature. When the addition was finished, the mixture showed a pH of about 11. The saponified dispersion was divided in five equal parts, and an aqueous solution of zinc sulfate (300 g/L) (1591 ml) was added to each part at 50°, 60°, 70°, 80° or 90° C. and the mixture was further stirred for 90 minutes. The product was collected, washed with water, filtered, dried at 75° C. for 72 hours and pulverized by the aid of a water-cooling type hammer mill to give zinc stearyl phosphate. The results are shown in Table 1.

Table 1

| | Reaction temperature (°C.) | Yield (%) | Apparent specific volume | |
|---|---|---|---|---|
| | | | First pulverization (ml/g) | Second pulverization (ml/g) |
| (a) | 50 | 96.5 | 6.5 | 8.0 |
| (b) | 60 | 96 | 9.3 | 11.0 |
| (c) | 70 | 96.2 | 8.8 | 10.2 |
| (d) | 80 | 97 | 8.0 | 9.7 |
| (e) | 90 | 97.1 | 4.0 | 4.5 |

As understood from Table 1, the reaction at 90° C. gave the product having only a low apparent specific volume. Even when this product was subjected to the second pulverization, fine powder could not be obtained.

EXAMPLE 7

Water (95 L) was added to stearyl phosphate (molar ratio of diester/monoester=1/2; acid value, 215.1 mg KOH/g) (4.0 kg) while heating at 70° C., whereby the stearyl phosphate was dispersed uniformly. An aqueous solution of sodium hydroxide (300 g/L) (2203 ml) was dropwise added to the mixture while keeping the said temperature. When the addition was finished, the mixture showed a pH of about 11. Further, stirring was continued at 70° C. for 60 minutes. An aqueous solution of zinc sulfate (300 g/L) (4211 ml) was added gradually at a temperature of 60° to 70° C. After the addition was finished, the mixture was stirred still for 90 minutes. The reaction mixture was treated as above. The product was dried at a variety of drying temperatures and each dried products was pulverized by the aid of a water-cooling type hammer mill under same conditions. The results are shown in Table 2.

Table 2

| | Drying temperature (°C.) | Apparent specific volume | |
|---|---|---|---|
| | | First pulverization (mg/g) | Second pulverization (ml/g) |
| (a) | 70 | 9.8 | 11.3 |
| (b) | 80 | 8.1 | 9.5 |
| (c) | 90 | 4.5 | 4.8 |
| (d) | 100 | 3.5 | 3.6 |

From the above results, it is understood that the drying at a temperature higher than 80° C. results in the depression of the apparent specific volume, which is not recovered even after the second pulverization.

EXAMPLE 8

In a reaction tank of 6 m³ in volume, water (2.5 m³) and sodium hydroxide (purity, 98%) (17.6 kg) were charged, and stearyl phosphate (molar ratio of diester/monoester=1/2.3; acid value, 221 mg KOH/g) (100 kg) was added thereto at 85° C. while stirring. After 60 minutes, water was added to make a temperature of 80° C. Then, a 12% aqueous solution of aluminum sulfate (224.6 kg) was gradually added thereto at a temperature of 75° to 80° C. in 15 minutes, followed by stirring at the same temperature for 90 minutes. The reaction mixture was filtered, and the collected cake was redispersed into water (about 3.5 m³), collected by filtration, dried at 75° C. for 48 hours and pulverized by the aid of a water-cooling type hammer mill to give aluminum stearyl phosphate (having 0.2 OH/Al) (104 kg) as white fine powder. Yield, about 100%. M.P., 215° to 225° C. Apparent specific volume, 7.6 ml/g. Elementary analysis: calcd., P=6.8%, Al=3.7%; found, P=6.9%, Al=3.4%.

EXAMPLE 9

In a 4 liter volume flask, water (1.5 L) and sodium hydroxide (purity, 94%) (17.1 g) were charged, and stearyl phosphate (molar ratio of diester/monoester=1/2.3; acid value, 221 mg KOH/g) (100 g) was added thereto at 90° C. while stirring. After the addition was finished, stirring was further continued for 60 minutes, and water was added thereto to make a temperature of 70° C. A 15% aqueous solution of aluminum sulfate (279.4 g) was dropwise added to the mixture at 65° to 70° C. in 10 minutes, followed by stirring for 60 minutes. Then, a 8% aqueous solution of sodium hydroxide (133.3 g) was added to the resulting mixture, and stirring was carried out at 65° to 70° C. for 60 minutes. The reaction mixture was filtered, and the collected cake was redispersed into water (about 2 L), collected by filtration, dried at 80° C. for 30 hours and pulverized in a mortar to give aluminum stearyl phosphate (having 1.2 OH/Al) (109 g) as white fine powder. Yield, 99%. M.P., >250° C. Apparent specific volume, 4.1 ml/g. Elementary analysis: calcd., P=6.4%, Al=5.4%; found, P=6.5%, Al=5.2%.

Comparative Example

Stearyl phosphate (molar ratio of diester/monoester=1/2.3; acid value, 221 mg KOH/g) (100 g) was heated to 120° C. under stirring, and zinc acetate dihydrate (90.8 g) was added thereto. Heating was continued in nitrogen stream under reduced pressure to make a temperature of 200° C. in 8 hours, during which acetic acid and water were distilled out. Since the melting point of the produced zinc stearyl phosphate was a temperature of 190° to 200° C., the uniform proceeding of the reaction became difficult with the elapse of time, and there was obtained the reaction product including unreacted materials, which showed an acid value of 95 mg KOH/g and had a smell of acetic acid. After cooling, the product was pulverized in a mortar to give particles of 2 ml/g in apparent specific volume.

Reference Example 1

Dispersibility of zinc stearyl phosphates having different apparent specific volumes to a vinyl chloride resin was examined.

A vinyl chloride resin ("Geon 130EP" manufactured by Nippon Zeon Co., Ltd.) (100 parts by weight) and zinc stearyl phosphate (molar ratio of diester/monoester=1/2) (2 parts by weight) were mixed together by the aid of a kneader at a temperature of 160° to 170° C. The gellation time of the resultant mixture was measured by the use of Brabender Plastograph (manufactured by Brabender OHG), and the dispersibility was determined on the gellation time. The results are shown in Table 3.

Table 3

| Apparent specific volume (ml/g) | Gellation time (min) | Judgement of dispersibility |
|---|---|---|
| 3.5 | 40 | Bad |
| 5.5 | 32 | Bad |
| 6.1 | 30 | Bad |
| 7.2 | 25 | Bad |
| 8.1 | 11 | Good |
| 9.8 | 10 | Good |

As understood from the above results, the one having a shorter gellation time (i.e. having an apparent specific volume of 8.1 ml/g or more) shows a higher dispersibility.

Reference Example 2

An acrylonitrile/butadiene/styrene copolymer resin ("Blendex 101" manufactured by Ube-Saikon K.K.) (100 parts by weight), 2,6-di-tert.-butyl-p-cresol (0.1 part by weight) as an antioxidant and a substance as shown in Table 4 (2 parts by weight) were mixed together to make a uniform mixture.

The resultant uniform mixture was kneaded by the aid of a mixing roll at a temperature as indicated in Table 4 for 5 minutes, and then the adhesion between the mixture and the roll was observed with the following criteria:

| Value | |
|---|---|
| 5 | not separable |
| 4 | hardly separable |
| 3 | somewhat separable |
| 2 | separable |
| 1 | easily separable |

The said uniform mixture was kneaded at 180° C. for 5 minutes by the aid of a mixing roll to make a sheet of 0.5 mm in thickness. The sheet was kept at 200° C. in a gear type aging tester for a certain period of time, and the produced coloring was observed for determination of the heat resistance.

The results are shown in Table 4, from which it is understandable that the product according to Example 7 (a) (i.e. according to the invention) can prevent the adhesion on the processing of the ABS resin and improve the heat resistance of the ABS resin much more than any other product.

Table 4

| | Apparent specific volume (ml/g) | Adhesion | | | Heat resistance | | |
|---|---|---|---|---|---|---|---|
| | | 180° C. | 200° C. | 220° C. | 30 min | 60 min | 75 min |
| Zinc stearyl phosphate according to Example 7 (a) | 11.3 | 2 | 3 | 4 | Colorless | Pale yellow | Pale yellow |
| Zinc stearyl phosphate according to Example 7 (a) but dried at 100° C. | 3.6 | 3 | 3 | 4 | Colorless | Pale yellow | Pale brown |
| Comparative Example | 2 | 4.5 | 4.5 | 5 | Pale yellow | Pale brown | Brown |
| Zinc | 10 | 4 | 4.5 | 5 | Color- | Pale | Pale |

Table 4-continued

| | Apparent specific volume (ml/g) | Adhesion | | | Heat resistance | | |
|---|---|---|---|---|---|---|---|
| | | 180° C. | 200° C. | 220° C. | 30 min | 60 min | 75 min |
| stearate | | | | | less | brown | brown |

What is claimed is:

1. A process for preparing metal salts of an alkyl phosphate corresponding to either one of the formulae:

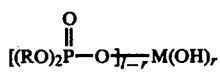

and

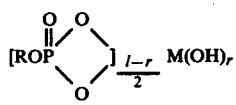

having a high apparent specific volume which comprises reacting an alkyl phosphate corresponding to either one of the formulae:

and

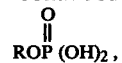

in the form of its alkali metal salt, with a metal salt of the formula: $M_nX_m$ in an aqueous medium at a temperature of from about 50° to 80° C., and recovering the reaction product from the reaction mixture, followed by filtration, water washing, drying and pulverizing, the operations on the recovery and thereafter being carried out at a temperature of not higher than 80° C.; in the above formulae R being an alkyl group of not less than 12 carbon atoms, M being an alkaline earth metal, aluminum or zinc, X being halogen, sulfate or nitrate, l being an integer corresponding to the atomic valency of M, r being the integer 0, 1 or 2, m being the integer 1, 2 or 3 and n being the integer 1 or 2.

2. The process of claim 1, wherein M is aluminum and the reaction is carried out in the presence of an alkali metal hydroxide.

3. The process of claim 1 wherein M is an alkaline earth metal.

4. The process of claim 1 wherein M is zinc.

* * * * *